(12) United States Patent
Carter et al.

(10) Patent No.: US 8,715,205 B2
(45) Date of Patent: May 6, 2014

(54) LOOP TIP WIRE GUIDE

(75) Inventors: Matthew P. Carter, Dobson, NC (US); David M. Hardin, Winston-Salem, NC (US); Jeffry S. Melsheimer, Springville, IN (US); Vihar C. Surti, Winston-Salem, NC (US)

(73) Assignee: Cook Medical Tecnologies LLC, Bloomington, IN (US)

( * ) Notice: Subject to any disclaimer, the term of this patent is extended or adjusted under 35 U.S.C. 154(b) by 822 days.

(21) Appl. No.: 11/841,175

(22) Filed: Aug. 20, 2007

(65) Prior Publication Data
US 2008/0051721 A1  Feb. 28, 2008

Related U.S. Application Data

(60) Provisional application No. 60/840,214, filed on Aug. 25, 2006.

(51) Int. Cl.
*A61M 25/09* (2006.01)

(52) U.S. Cl.
CPC .......... *A61M 25/0905* (2013.01); *A61M 25/09* (2013.01)
USPC ........................................ 600/585

(58) Field of Classification Search
CPC .................. A61M 25/0905; A61M 25/09016; A61M 25/09
USPC .............................. 600/585, 434
See application file for complete search history.

(56) References Cited

U.S. PATENT DOCUMENTS

| 3,791,387 | A | | 2/1974 | Itoh |
| 3,890,977 | A | | 6/1975 | Wilson |
| 4,176,662 | A | | 12/1979 | Frazer |
| 4,207,872 | A | | 6/1980 | Meiri et al. |
| 4,281,660 | A | | 8/1981 | Fujiwara |
| 4,310,789 | A | | 1/1982 | Mank et al. |
| 4,326,530 | A | | 4/1982 | Fleury, Jr. |
| 4,447,227 | A | | 5/1984 | Kotsanis |
| 4,545,390 | A | | 10/1985 | Leary |
| 4,729,384 | A | * | 3/1988 | Bazenet .................... 600/504 |
| 4,800,890 | A | | 1/1989 | Cramer |

(Continued)

FOREIGN PATENT DOCUMENTS

| EP | 0 667 115 A1 | 1/1995 |
| EP | 0 827 712 A2 | 11/1999 |

(Continued)

OTHER PUBLICATIONS

International Search Report mailed Jan. 17, 2008 for International Application No. PCT/US2007/076305.

(Continued)

*Primary Examiner* — Sean Dougherty
*Assistant Examiner* — Michael C Stout
(74) *Attorney, Agent, or Firm* — Brinks Gilson & Lione

(57) ABSTRACT

An elongate medical device configured for navigation through a lumen is provided. The device includes an elongate shaft having a proximal portion and a distal portion. The distal portion includes a first interlocking connector. The device further includes a loop portion operably connected to the distal portion. The loop portion includes a second interlocking connector configured for connecting to the first interlocking connector. A medical system is also provided including a catheter and a wire guide. A method of making a wire guide is provided.

20 Claims, 8 Drawing Sheets

(56) References Cited

U.S. PATENT DOCUMENTS

| | | | |
|---|---|---|---|
| 4,824,435 A * | 4/1989 | Giesy et al. ................ 604/500 |
| 5,003,990 A * | 4/1991 | Osypka ........................ 600/585 |
| 5,037,391 A | 8/1991 | Hammerslag et al. |
| 5,054,501 A | 10/1991 | Chuttani et al. |
| 5,069,217 A | 12/1991 | Fleischhacker, Jr. |
| 5,078,716 A | 1/1992 | Doll |
| 5,109,867 A * | 5/1992 | Twyford, Jr. ................ 600/585 |
| 5,114,402 A | 5/1992 | McCoy |
| 5,131,407 A * | 7/1992 | Ischinger et al. ........... 600/585 |
| 5,133,364 A * | 7/1992 | Palermo et al. ............. 600/585 |
| 5,211,636 A | 5/1993 | Mische |
| 5,221,270 A | 6/1993 | Parker |
| 5,246,009 A * | 9/1993 | Adams ........................ 600/585 |
| 5,247,942 A * | 9/1993 | Prather et al. ............... 600/585 |
| 5,271,415 A * | 12/1993 | Foerster et al. ............. 600/585 |
| 5,282,478 A * | 2/1994 | Fleischhaker et al. ....... 600/585 |
| 5,300,048 A | 4/1994 | Drewes, Jr. et al. |
| 5,334,168 A | 8/1994 | Hemmer |
| 5,337,732 A | 8/1994 | Grundfest et al. |
| 5,345,925 A | 9/1994 | Allred, III et al. |
| 5,349,964 A | 9/1994 | Imran et al. |
| 5,357,978 A * | 10/1994 | Turk ............................ 600/585 |
| 5,358,479 A | 10/1994 | Wilson |
| 5,365,943 A * | 11/1994 | Jansen ......................... 600/585 |
| 5,376,083 A | 12/1994 | Mische |
| 5,387,219 A | 2/1995 | Rappe |
| 5,398,670 A | 3/1995 | Ortiz et al. |
| 5,421,348 A * | 6/1995 | Larnard ........................ 600/585 |
| 5,433,200 A | 7/1995 | Fleischhacker, Jr. |
| 5,490,845 A | 2/1996 | Racz |
| 5,498,249 A | 3/1996 | Quinn |
| 5,513,650 A * | 5/1996 | Johansen .................... 600/508 |
| 5,522,819 A | 6/1996 | Graves et al. |
| 5,531,685 A | 7/1996 | Hemmer et al. |
| 5,595,565 A | 1/1997 | Treat et al. |
| 5,604,531 A | 2/1997 | Iddan et al. |
| 5,613,973 A | 3/1997 | Jackson et al. |
| 5,643,281 A | 7/1997 | Suhocki et al. |
| 5,685,312 A * | 11/1997 | Yock ............................ 600/462 |
| 5,728,122 A | 3/1998 | Leschinsky et al. |
| 5,730,704 A | 3/1998 | Avitall |
| 5,800,453 A * | 9/1998 | Gia .............................. 606/191 |
| 5,813,405 A * | 9/1998 | Montano et al. ............ 600/585 |
| 5,824,031 A | 10/1998 | Cookston et al. |
| 5,836,947 A | 11/1998 | Fleischman et al. |
| 5,879,295 A | 3/1999 | Li et al. |
| 5,885,381 A | 3/1999 | Mitose et al. |
| 5,885,741 A | 3/1999 | Akamastu et al. |
| 5,891,130 A * | 4/1999 | Palermo et al. ............. 606/1 |
| 5,904,648 A | 5/1999 | Arndt et al. |
| 6,007,482 A | 12/1999 | Madni et al. |
| 6,056,743 A | 5/2000 | Ellis et al. |
| 6,059,719 A * | 5/2000 | Yamamoto et al. .......... 600/127 |
| 6,099,546 A * | 8/2000 | Gia .............................. 606/191 |
| 6,102,918 A | 8/2000 | Kerr |
| 6,162,171 A | 12/2000 | Ng et al. |
| 6,190,382 B1 | 2/2001 | Ormsby et al. |
| 6,193,708 B1 | 2/2001 | Ken et al. |
| 6,203,525 B1 | 3/2001 | Whayne et al. |
| 6,203,547 B1 * | 3/2001 | Nguyen et al. .............. 606/102 |
| 6,206,852 B1 | 3/2001 | Lee |
| 6,259,938 B1 * | 7/2001 | Zarychta et al. ............. 600/380 |
| 6,277,139 B1 | 8/2001 | Levinson et al. |
| 6,290,693 B1 * | 9/2001 | Jung et al. .................... 604/535 |
| 6,348,045 B1 * | 2/2002 | Malonek et al. ............. 604/270 |
| 6,371,970 B1 | 4/2002 | Khosravi et al. |
| 6,379,319 B1 * | 4/2002 | Garibotto et al. ............ 600/585 |
| 6,454,758 B1 | 9/2002 | Thompson et al. |
| 6,464,699 B1 | 10/2002 | Swanson |
| 6,500,167 B1 | 12/2002 | Webster, Jr. |
| 6,530,913 B1 | 3/2003 | Giba et al. |
| 6,551,302 B1 | 4/2003 | Rosinko et al. |
| 6,591,144 B2 | 7/2003 | Pigott |
| 6,592,581 B2 | 7/2003 | Bowe |
| 6,602,208 B2 * | 8/2003 | Jafari ........................... 600/585 |
| 6,616,617 B1 | 9/2003 | Ferrera et al. |
| 6,620,179 B2 | 9/2003 | Boock et al. |
| 6,720,402 B2 | 4/2004 | Langer et al. |
| 6,730,058 B2 | 5/2004 | Hayzelden |
| 6,824,543 B2 * | 11/2004 | Lentz ........................... 606/21 |
| 7,288,074 B2 * | 10/2007 | Swain et al. ................. 600/585 |
| 7,371,249 B2 * | 5/2008 | Douk et al. .................. 606/200 |
| 7,993,329 B2 * | 8/2011 | Howell et al. ............... 606/2.5 |
| 2001/0031970 A1 * | 10/2001 | Heuser et al. ................ 606/108 |
| 2002/0010426 A1 | 1/2002 | Clayman et al. |
| 2002/0016604 A1 | 2/2002 | Boock et al. |
| 2002/0032455 A1 | 3/2002 | Boock et al. |
| 2002/0087100 A1 * | 7/2002 | Onuki et al. ................. 600/585 |
| 2002/0123698 A1 * | 9/2002 | Garibotto et al. ............ 600/585 |
| 2004/0006311 A1 * | 1/2004 | Shchervinsky ............. 604/164.01 |
| 2004/0016849 A1 | 1/2004 | Jakubowski et al. |
| 2004/0030259 A1 | 2/2004 | Dae et al. |
| 2004/0030350 A1 * | 2/2004 | Griego et al. ................ 606/167 |
| 2004/0082859 A1 * | 4/2004 | Schaer ......................... 600/459 |
| 2004/0082881 A1 | 4/2004 | Grewe et al. |
| 2004/0106897 A1 | 6/2004 | Thompson et al. |
| 2004/0111020 A1 | 6/2004 | Long |
| 2004/0111082 A1 * | 6/2004 | Howell et al. ............... 606/2.5 |
| 2004/0125139 A1 | 7/2004 | Beck et al. |
| 2004/0193032 A1 | 9/2004 | Mogul |
| 2004/0193205 A1 | 9/2004 | Burgermeister |
| 2004/0199087 A1 | 10/2004 | Swain et al. |
| 2004/0199088 A1 | 10/2004 | Bakos et al. |
| 2004/0215208 A1 * | 10/2004 | Foushee et al. .............. 606/108 |
| 2004/0225233 A1 * | 11/2004 | Frankowski et al. ........ 600/585 |
| 2004/0236346 A1 * | 11/2004 | Parker .......................... 606/108 |
| 2004/0243168 A1 * | 12/2004 | Ferrera et al. ................ 606/191 |
| 2005/0027243 A1 | 2/2005 | Gibson et al. |
| 2005/0038412 A1 | 2/2005 | Rabiner et al. |
| 2005/0043779 A1 | 2/2005 | Wilson |
| 2005/0070821 A1 * | 3/2005 | Deal et al. .................... 600/585 |
| 2005/0080356 A1 | 4/2005 | Dapolito et al. |
| 2005/0096590 A1 | 5/2005 | Gullickson et al. |
| 2005/0165277 A1 * | 7/2005 | Carrillo et al. ............... 600/154 |
| 2005/0228222 A1 * | 10/2005 | Furumi ........................ 600/101 |
| 2005/0261663 A1 * | 11/2005 | Patterson et al. ............ 604/508 |
| 2005/0288545 A1 * | 12/2005 | Matsumoto et al. ......... 600/101 |
| 2006/0100544 A1 | 5/2006 | Ayala et al. |
| 2006/0100545 A1 * | 5/2006 | Ayala et al. .................. 600/585 |
| 2006/0189975 A1 * | 8/2006 | Whayne et al. .............. 606/41 |
| 2007/0060997 A1 | 3/2007 | De Boer |
| 2007/0083253 A1 | 4/2007 | Fischell et al. |
| 2007/0135825 A1 * | 6/2007 | Binmoeller ................... 606/153 |
| 2007/0162047 A1 * | 7/2007 | Gasche ........................ 606/113 |
| 2007/0185414 A1 * | 8/2007 | Urbanski et al. ............ 600/585 |
| 2007/0185416 A1 * | 8/2007 | Melsheimer .................. 600/585 |
| 2007/0299367 A1 * | 12/2007 | Melsheimer et al. ........ 600/585 |
| 2008/0051676 A1 * | 2/2008 | Melsheimer .................. 600/585 |
| 2008/0051721 A1 | 2/2008 | Carter et al. |
| 2008/0064988 A1 * | 3/2008 | Carter et al. ................. 600/585 |
| 2009/0012475 A1 | 1/2009 | Onuki et al. |
| 2011/0257476 A1 * | 10/2011 | Belafsky ....................... 600/104 |

FOREIGN PATENT DOCUMENTS

| | | |
|---|---|---|
| EP | 1 346 747 A2 | 9/2003 |
| EP | 1 532 999 A2 | 11/2004 |
| FR | 2511600 | 2/1983 |
| FR | 2625437 | 7/1989 |
| GB | 2 103 936 A | 3/1983 |
| JP | 62-116746 U | 5/1987 |
| JP | 07088191 A | 4/1995 |
| JP | 2006-192294 A | 7/2006 |
| WO | WO 94/05200 A1 | 3/1994 |
| WO | WO 97/31677 A1 | 9/1997 |
| WO | WO 98/11896 A1 | 3/1998 |
| WO | WO 98/19608 A1 | 5/1998 |
| WO | WO 99/30610 A1 | 6/1999 |
| WO | WO 99/34726 A1 | 7/1999 |
| WO | WO 99/53827 A1 | 10/1999 |
| WO | WO 00/22975 A1 | 4/2000 |
| WO | WO 00/44275 A1 | 8/2000 |
| WO | WO 01/03764 A1 | 1/2001 |
| WO | WO 01/08548 A1 | 2/2001 |

(56) References Cited

FOREIGN PATENT DOCUMENTS

| WO | WO 01/08742 A1 | 2/2001 |
|----|----|----|
| WO | WO 01/67967 A1 | 9/2001 |
| WO | WO 02/070061 A1 | 9/2002 |
| WO | WO 2004/050161 A1 | 6/2004 |
| WO | WO 2004/089456 A1 | 10/2004 |
| WO | WO 2006/039216 A2 | 4/2006 |
| WO | WO 2006/039217 A1 | 4/2006 |

OTHER PUBLICATIONS

International Search Report mailed Feb. 15, 2008 for International Application No. PCT/US2007/077072.

Long, Gary, Ph.D., et al.; "The Cath-Cam: a new concept in colonoscopy;" Gastrointestinal Endoscopy, vol. 64, No. 6, Dec. 2006, pp. 997-1001.

Mosse, C.A., Ph.D., et al., "Technical Advances and Experimental Devices for Enteroscopy;" Gastrointest Endosc Clin N Am., vol. 9, No. 1, Jan. 1999, pp. 145-161.

Hodgson et al., *Shape memory alloys*, [online], [retrieved on Dec. 9, 2009]. Retrieved from Johnson Matthey database using Internet <URL: http://www.jmmedical.com/html/_shape_memory_alloys_.html>.

Lin, *Shape memory alloys and Their Applications* (1996, 1998), [online], [retrieved on Dec. 5, 2005]. Retrieved from Stanford University database using Internet <URL: http://www stanford.edu/~richlin/sma/sma.html>.

*Shape memory alloys* (2001), [online], [retrieved on Dec. 9, 2005]. Retrieved from University of Alberta database using Internet <URL: http://www.cs.ualberta.ca/~database/MEMS/sma_mems/sma.html>.

*Two-Way Memory*, [online], [retrieved on Dec. 9, 2005]. Retrieved from Johnson Matthey database using Internet <URL: http://www.jmmedical.com/html/2_way_memory.html>.

\* cited by examiner

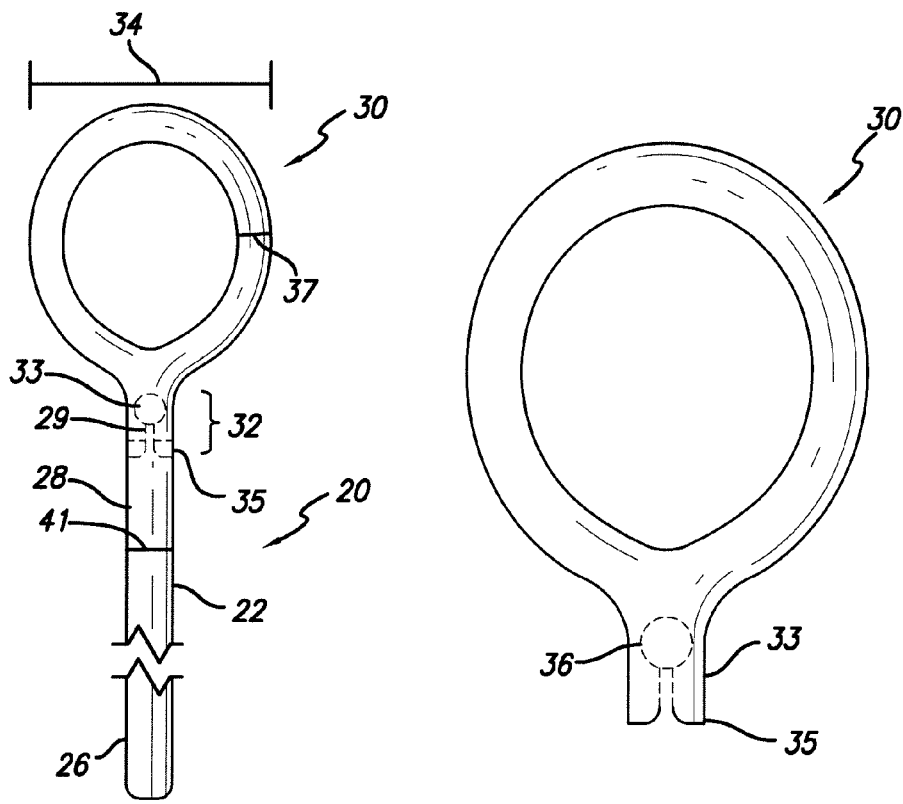
FIG. 1
FIG. 2A
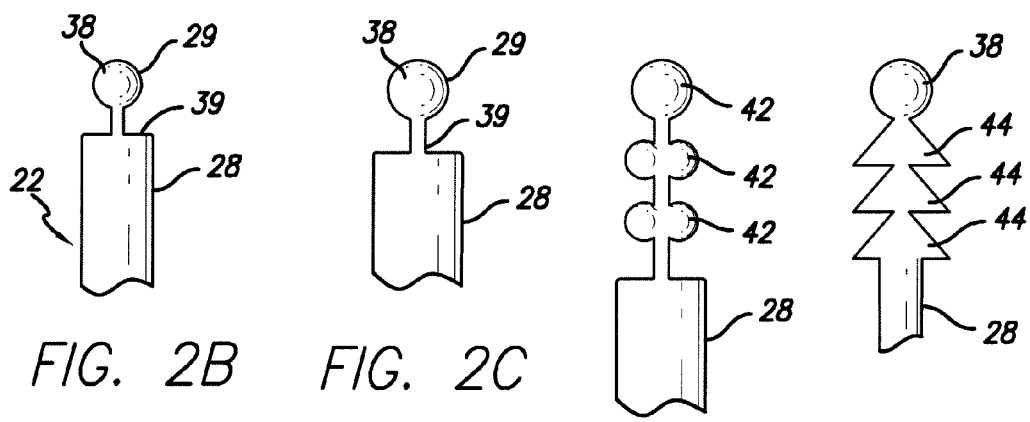
FIG. 2B   FIG. 2C   FIG. 2D   FIG. 2E

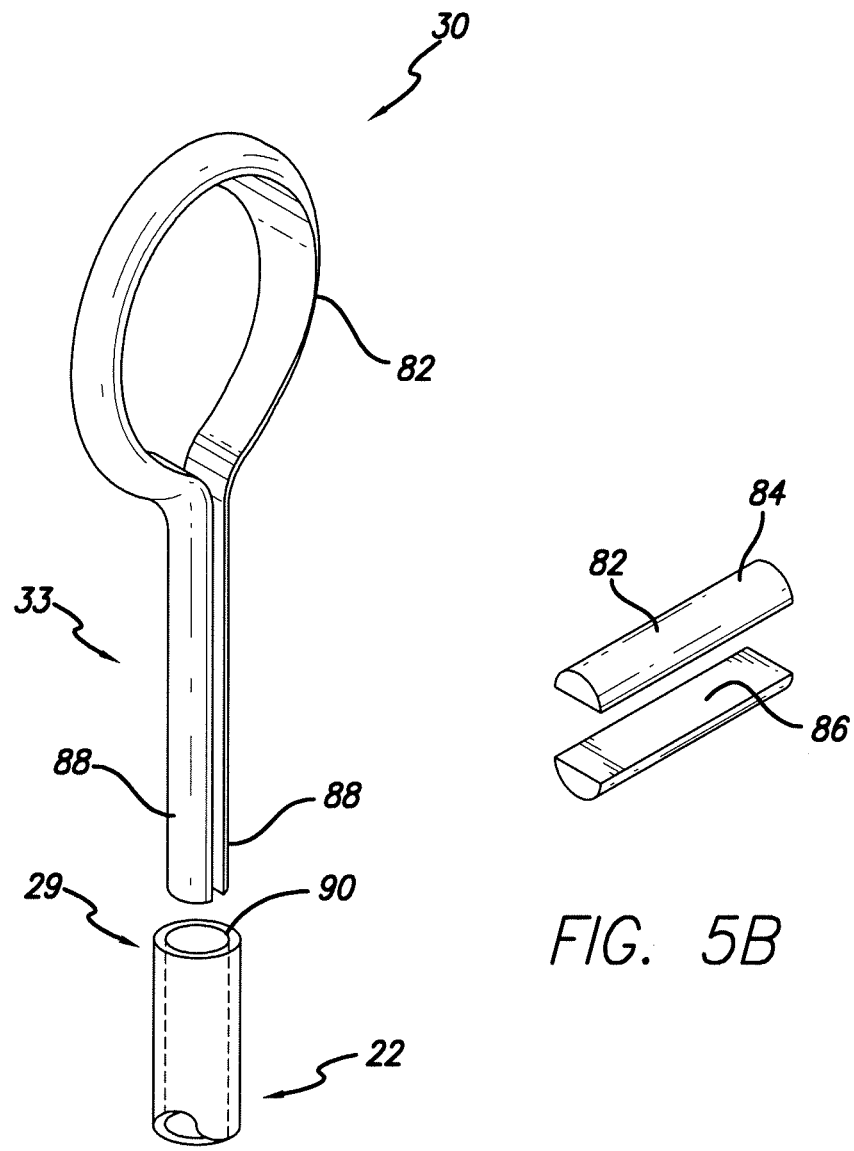

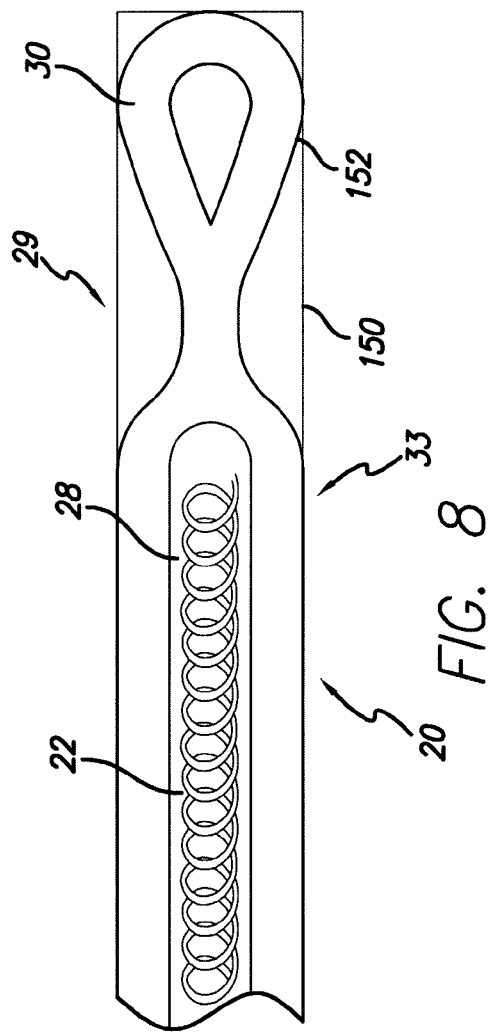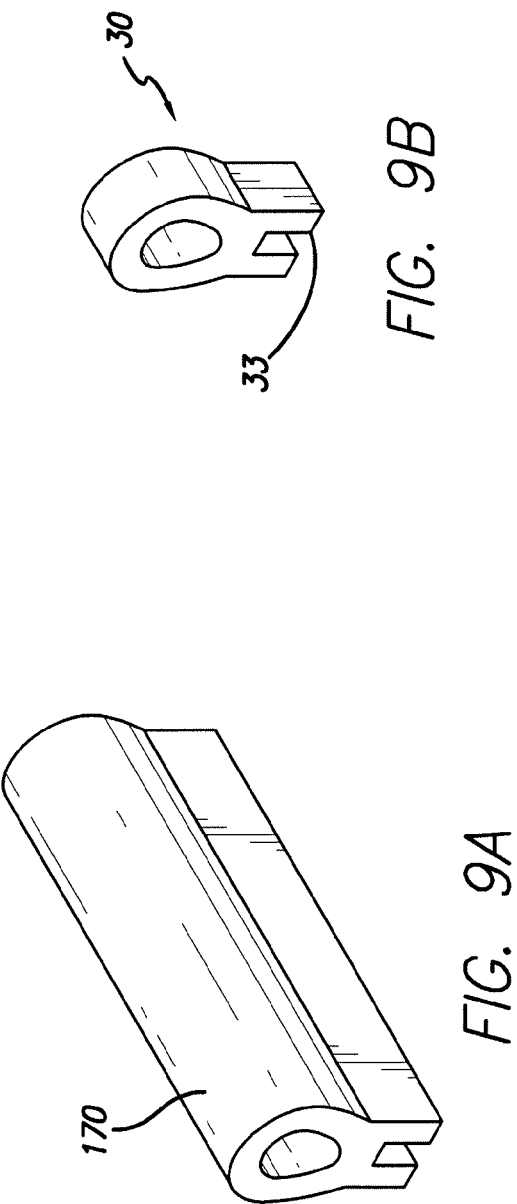

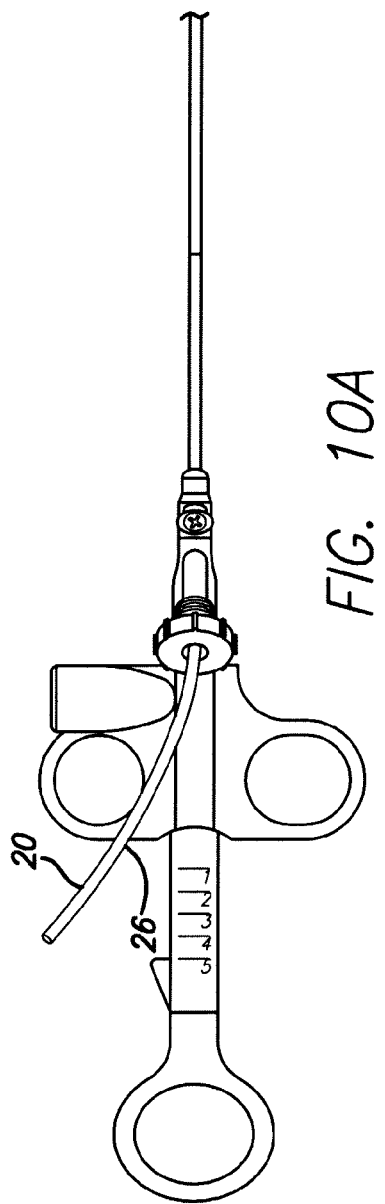
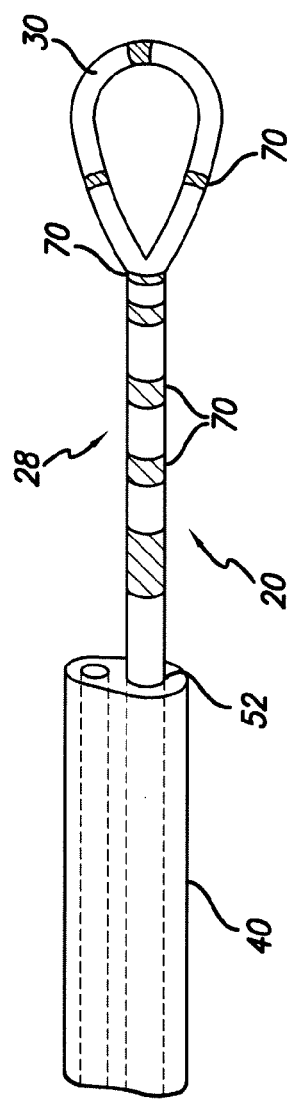
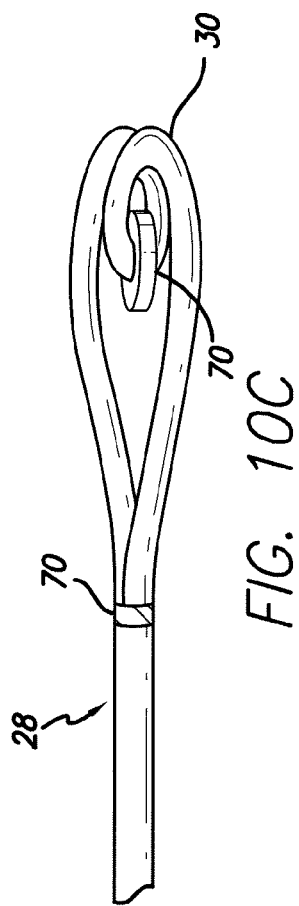

LOOP TIP WIRE GUIDE

RELATED APPLICATIONS

This application claims the benefit of U.S. Provisional Application No. 60/840,214 filed Aug. 25, 2006, which is incorporated by reference herein in its entirety.

BACKGROUND

1. Technical Field

This invention relates to wire guides used in the placement of medical devices, and more particularly to wire guides having a loop tip.

2. Background Information

Wire guides are elongate flexible members used to provide a path along which another medical device can be moved. The path provided by the wire guide can be used to navigate another medical device, such as a catheter through a body vessel. The use of wire guides to define such a path is known in the art. Briefly, a wire guide is navigated through a body lumen toward a point of treatment. Once positioned within the lumen, a therapeutic or diagnostic device, (i.e., a catheter) may be advanced over the wire guide to the target site and the desired therapeutic or diagnostic steps may be performed. The wire guide provides an established path for placing other devices and eliminates the need for performing delicate navigation procedures for each device passed into the body lumen, for example when additional procedures are performed.

During placement of the wire guide, an operator must navigate the wire guide through a tortuous pathway in the body lumen due to the presence of natural bends and/or curves, or unnatural impediments, such as tumors, build-ups, and/or strictures. The presence of a tortuous path may make navigation of a wire guide through the path difficult, for example, the tip of the wire guide may get bent away from the desired path or caught in a stricture, or in some cases even perforate the wall of the lumen, etc. making further navigation into the lumen difficult or impossible.

The prior art contains many examples of wire guides having straight, flexible tips intended to aid in navigation of tortuous body lumens. The presence of a straight tip, however, may make navigation more difficult. For example, upon encountering an impediment, the straight tip may bend (reflex) into the lumen wall and become caught. Contact of the straight tip with the lumen wall may prevent the wire guide from advancing further into the lumen as well as possibly damaging the lumen wall.

What is needed is an improved wire guide tip for navigating a tortuous body lumen where the improved wire guide includes a loop tip configured for facilitating navigation and reducing trauma to the lumen wall during advancement of the wire guide.

BRIEF SUMMARY

The various preferred embodiments provide significant improvements and advantages over conventional straight wire guide tips.

According to one aspect of the present invention, an elongate medical device configured for navigation through a bodily lumen is provided. The device includes an elongate shaft having a proximal portion and a distal portion. The distal portion includes a first interlocking connector. The device further includes a loop portion operably connected to the distal portion. The loop portion includes a second interlocking connector configured for connecting to the first interlocking connector.

According to another aspect of the present invention, an elongate medical system is provided. The system includes a catheter and a wire guide extending from a distal portion of the catheter. The wire guide includes an elongate shaft having a proximal portion and a distal portion. The distal portion of the shaft includes a first interlocking connector. The wire guide further includes a loop portion having a second interlocking connector configured for connecting to the first interlocking connector on the shaft.

In another aspect of the present invention, a method of manufacturing a wire guide having a loop tip is provided. The method includes forming an elongate shaft having a proximal portion and a distal portion. The distal portion has a first interlocking connector. The method further includes forming a loop structure having a second interlocking connector. The first interlocking connector of the shaft is connected to the second interlocking connector of the loop.

The foregoing paragraphs have been provided by way of general introduction, and are not intended to limit the scope of the following claims. The presently preferred embodiments, together with further advantages will be best understood by reference to the following detailed description taken in conjunction with the accompanying drawings.

BRIEF DESCRIPTION OF THE DRAWINGS

Embodiments of the present invention will now be described by way of example with reference to the accompanying drawings, in which:

FIG. 1 is a partial side view of a wire guide having a loop tip according to the present invention;

FIG. 2A is a partial side view of an embodiment of a loop portion having a receiving structure at a loop interlocking connector;

FIGS. 2B-2E are partial side views of alternative connections at a shaft interlocking connector;

FIG. 5A is a partial side view of an alternative embodiment of the wire guide shown in FIG. 1;

FIG. 5B is a partial perspective view of a section of the loop tip of the wire guide shown in FIG. 5A;

FIG. 8 is a partial side view of the wire guide illustrating an alternative method of formation of the loop tip;

FIG. 9A is a perspective view of tubing used to form a loop;

FIG. 9B is a perspective view of a loop formed from the tubing shown in FIG. 9A;

FIG. 10A is a side view of a catheter comprising a handle with a proximal portion of a wire guide extending from an exit port;

FIG. 10B is a side view of a proximal portion of the catheter shown in FIG. 10A with a wire guide disposed through a lumen thereof;

FIG. 10C is a side view of a proximal portion of an alternative embodiment of the proximal portion shown in FIG. 10B;

DETAILED DESCRIPTION OF THE INVENTION

Figure 3A:
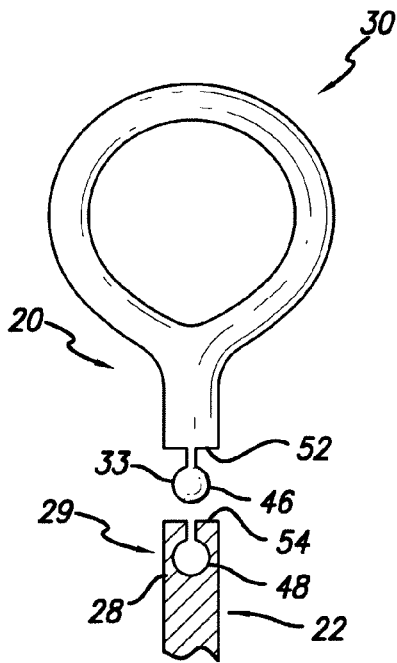
FIG. 3A is a partial cross-sectional side view of the wire guide shown in FIG. 1 showing the interlocking connectors prior to connection.

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances details have been omitted, which are not necessary for an understanding of the present invention, such as conventional details of fabrication and assembly.

As used in the specification, the terms proximal and distal should be understood as being in the terms of a physician using the wire guide. Hence the term distal means the portion of the wire guide which is farthest from the physician and the term proximal means the portion of the wire guide which is nearest to the physician.

FIG. 1 illustrates a wire guide 20 according to the present invention. The wire guide 20 includes an elongate shaft 22 having a proximal portion 26, a distal portion 28 and a loop 30. The distal portion 28 may include a first connector 29 that is connectable to the loop 30 of the wire guide 20. The loop 30 may include a loop connector 33 that is sized and shaped to fit together with the shaft connector 29. The connection between the loop connector 33 and the shaft connector 29 will provide for transmission of torque so that the loop 30 may be steered and directed through the pathway and change direction if necessary. The connectors 29 and 33 may have any size and shape that can be engaged together to join the shaft 22 and the loop 30 at a connecting structure 32 of the wire guide 20 as will be discussed in greater detail below. In some embodiments, the first connector 29 may be releasably interlocking with the loop connector 33. As shown, the loop 30 is generally curvilinear in shape, although other shapes are possible. In some embodiments, the loop is generally oval in shape. Additional shapes include, but are not limited to round, arched, and parabolic. The cross-sectional shape of the loop 30 or portions thereof, may be any shape. For example, the cross-sectional shape of the loop 30 may be rectangular, arched rectangular, circular, teardrop, oval and the like. See for example FIGS. 4B and 5B. The thickness of the material and the type of material used to form the loop 30 may be varied to provide flexibility for the loop 30 as will be understood by one skilled in the art. The loop 30 may be deformable as the loop 30 moves through a tortuous body lumen, including past any impediments that may be in the lumen such as a tumor or a sphincter. The shape of the loop 30 refers to the general shape in a pre-advancement state. The loop 30 has a diameter 34 measured at the widest portion of the loop 30. The loop 30 may also be adapted for application to any elongate medical device, such as a catheter. In some embodiments, the proximal portion 26 of the wire guide 20 has a diameter 41 that is smaller than the diameter 34 of the loop 30.

As shown in FIG. 1, the connecting structure 32 is formed where the connector 29 of the shaft 22 joins the connector 33 of the loop 30. The connecting structure 32 may have a smooth outer surface 35 for facilitating passage through the body lumen. Exemplary connecting configurations are discussed below, however any configuration for connecting the loop 30 and the shaft 22 may be used. By way of non-limiting example, connecting configurations where the first connector 29 interlocks with the second connector 33 may include snap-fit, threads, clips, adhesives and magnets. In some embodiments, the loop 30 may be completely removed from the shaft 22 after the loop 30 has traveled to the desired position in the bodily lumen. For example, the loop 30 may be removed by retracting the loop 30 back toward an end 53 of a catheter 40 so that contact of the loop 30 against the end 53 detaches the loop 30 from the shaft 22 (catheter shown in FIG. 10B). The loop 30 configuration may be designed so that the loop is removable by pulling the loop 30 back against the catheter, for example, using a ball and socket configuration. The loop 30 may also include a coating (discussed below) over the connection between the loop 30 and the shaft 22 that is absorbable and is made to degrade after a desired amount of time after exposure to bodily fluids. The loop 30 may be bioabsorbable and/or may be removed in the gastrointestinal tract where the loop 30 may pass through and be eliminated.

FIGS. 2A-2E and 3A-3C illustrate embodiments showing different sizes, shapes and forms for providing the connector 29 on the shaft 22 and the connector 33 on the loop 30. For example, FIG. 2A illustrates the loop 30 having the connector 33 formed from a spherically-shaped receiving structure 36 that is sized and shaped to engage with a connector 29 that is formed from a spherically-shaped protruding tip 38 extending on a stem 39 (FIG. 2B), e.g. a ball and socket connection. This configuration may be designed for snap-fit connection with the receiving structure 36 being sufficiently flexible to open to receive the protruding tip 38 and to close when the tip 38 is in the receptacle 36.

Alternative configurations for the connector 29 are shown in FIG. 2C-2E that will join together with a correspondingly shaped connector 33 on the loop 30 (not shown). For example, as shown in FIG. 2C, the stem 39 may be extended further distally as compared to the stem 39 shown in FIG. 2A and may also include the spherically-shaped protruding tip 38. The connector 33 of the loop 30 will include a correspondingly shaped receptacle. As shown in FIG. 2D, the connector 29 of the shaft 22 may also be formed from a plurality of spherically-shaped protrusions 42 and have a corresponding number of spherically-shaped receiving structures formed in the connector 33 of the loop 30. In another configuration, shown in FIG. 2E, the connector 29 may be formed from a plurality of conically shaped protrusions 44 and may further include the spherically-shaped protruding tip 38. As one skilled in the art will understand, any shape and number of protrusions may be formed on the connector 29 to permit the connector 29 to be joined with a correspondingly shaped receptacle formed on in the connector 33 of the loop 30.

Figure 3B:
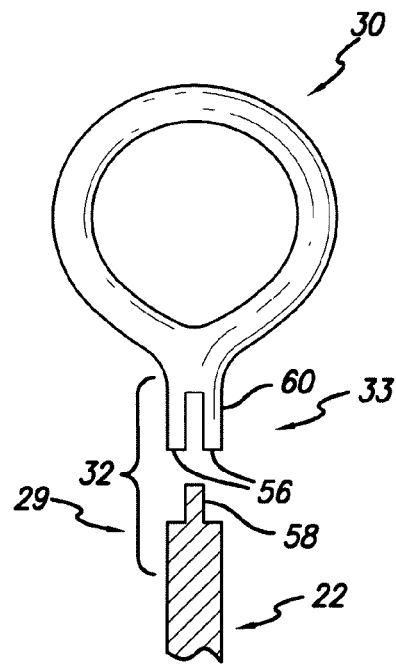
FIG. 3B is a partial side view of the an alternative embodiment of the interlocking connectors shown in FIG. 3A.
Figure 3C:
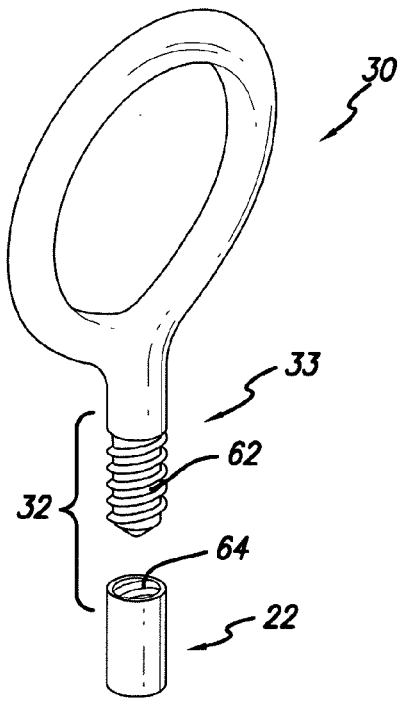
FIG. 3C is a partial side view of an alternative embodiment of the interlocking connectors shown in FIG. 3A.

FIGS. 3A-3C illustrate alternative configurations for the connector 29 of the shaft 22 and the connector 33 of the loop 30. For example, as shown in FIG. 3A, the loop 30 includes a connector 33 having a spherically-shaped protrusion 46 and the shaft 22 includes a connector 29 having a spherically-shaped receptacle 48. The protrusion 47 and the receptacle 48 fit together so that a proximal portion 52 of the loop 30 abuts a distal portion 54 of the shaft 22 forms the outer surface 35 of the wire guide 20. Similarly, the loop 30 and the shaft 22 may be connected together by protrusions 56 extending from the loop 30 that interlocks with one or more protrusions 58 extending from the shaft 22 as shown in FIG. 3B. The protrusions 56 and 58 are sized and shaped to fit together at the connecting structure 32. The protrusions 56 and 58 may be any shape and may include a curved outer surface 60 to form a smooth connecting structure 32. FIG. 3C illustrates another alternative configuration for connecting the loop 30 to the shaft 22. The loop 30 includes a connector 33 having an externally threaded proximal portion 62. The shaft 22 includes a interlocking connector 29 having an internally threaded portion 64 for joining with the proximal portion 62 of the loop at the connecting structure 32. Alternative embodiments may include an externally threaded connector 29 on the shaft 22 and an internally threaded connector 33 on the loop 30. In some embodiments, the connector 29 of the shaft 22 and the connector 33 of the loop 30 will join together and form the smooth outer surface 35 (as shown in FIG. 1) to facilitate passage of the wire guide 20 through the body lumen.

Figure 4A:
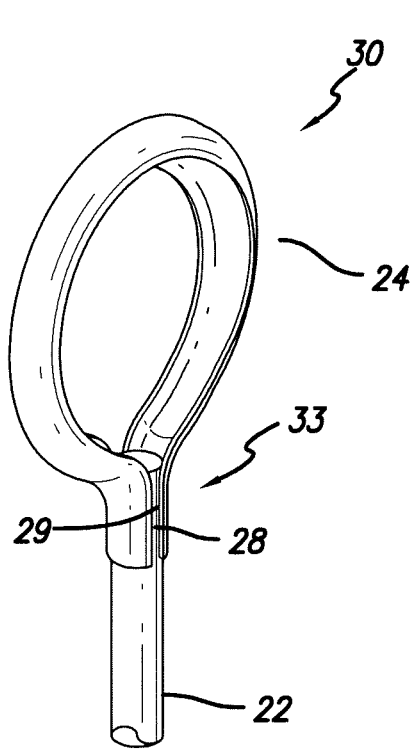
FIG. 4A is a partial side view of an alternative embodiment of the wire guide shown in FIG. 1.
Figure 4C:
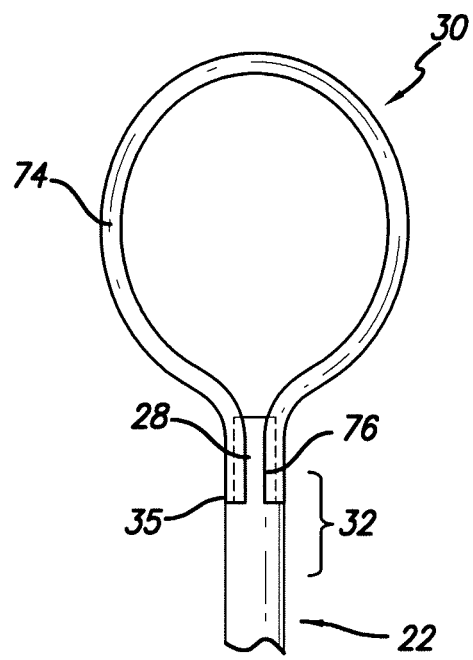
FIG. 4C is a partial side view of an alternative connection for the wire guide shown in FIG. 4A.
Figure 4B:
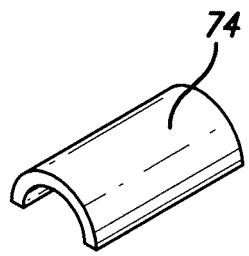
FIG. 4B is a partial perspective view of a section of the loop tip of the wire guide shown in FIG. 4A.

In some embodiments, the loop 30 may be externally connected to the distal portion 28 of the shaft 22. As shown in FIGS. 4A-4C, the loop 30 may be formed from a curved, rectangular ribbon member 74 that is shaped to curve around the connector 29 on the shaft 22 of the wire guide 20 and form a connector 33. A portion of the ribbon member 74 is shown in FIG. 4B illustrating the curve of the ribbon member itself. The curved shape of the ribbon member 74 forming the loop 30 may help navigating the tortuous lumen and provide flexibility as well as enough rigidity to resist buckling while the wire guide 20 moves forward. The loop 30 shown in FIG. 4C may be configured to curve around the distal portion 28 of the shaft 22 where a portion 76 of the distal portion 28 is recessed with respect to the outer surface 35 at the connector 29. In the embodiment shown in FIG. 4C, the outer surface 35 of the wire guide 20 is configured to provide a smooth surface.

In some embodiments, the loop 30 may be formed from a semi-circularly shaped member 82 where the curved portion 84 of the semicircle extends outward and the flattened portion 86 faces inward. The loop 30 may be formed by positioning end regions 88 of the semicircle member 82 with the flattened portions 86 against each other wherein the loop 30 extends between the end regions. As shown in FIG. 5A, the flattened portion 86 of the end regions 88 may be abutted against each other to form the connector 33 and inserted into an opening 90 at the connector 29 in the shaft 22. FIG. 5B illustrates an exploded view of adjacent flattened portions 86 that may be positioned against each other to form the loop 30 shown in FIG. 5A. The opening 90 may be sized and shaped to receive the end regions 88 of the loop 30 to form the wire guide 20. Alternatively, the end regions 88 may be connected to the shaft 22 using any configuration.

Figure 6A:
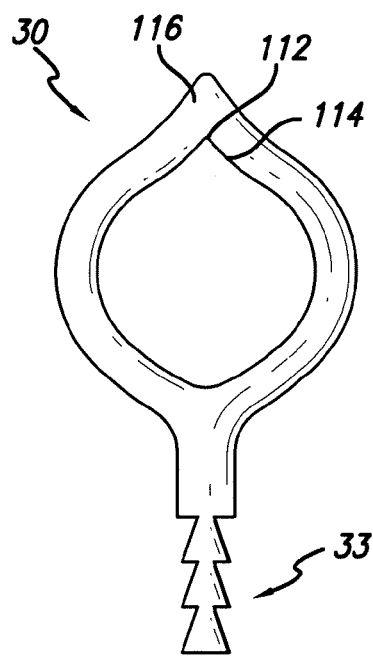
FIG. 6A is a partial side view of an alternative embodiment of the loop tip wire guide of the present invention.
Figure 6B:
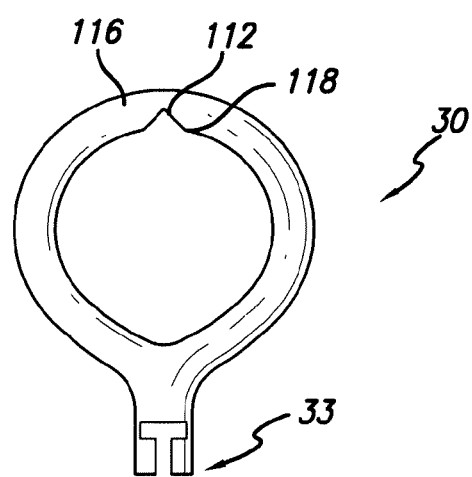
FIG. 6B is a partial side view of an alternative embodiment of the loop tip wire guide of the present invention.

In some embodiments, the loop 30 may include a folding region 112 to facilitate folding of the loop 30, for example, for withdrawing the loop 30 into a catheter. As shown in FIG. 6A, the folding region 112 may be provided by forming an arch 114 at a leading edge 116 of the loop 30 in the direction of navigation. The folding region 112 may also be a notch 118 cut into the leading edge 116 of the loop 30 as shown in FIG. 6B. In these embodiments having the folding region 112, the arch 114 or notch 118 may be positioned so that the loop 30 moves forward through the body lumen by flexing with the contours of the lumen and maintaining the loop configuration without folding. When the loop 30 is withdrawn from the body lumen and into a catheter (see FIGS. 10A and 10B), the loop 30 may fold into a narrower configuration by bending inwardly at the arch 114 or the notch 118 for facilitating withdrawal of the wire guide 20. The folding region 112 may be provided with any of the loop configurations described herein. The folding region 112 may be provided by including a region in the loop 30 that is more flexible at the folding region 112 in comparison to the surrounding loop portions. For example, the material forming the folding region 112 may be more flexible, have a reduced thickness, or serrations or cut away portions on the inner surface of the loop 30.

Figure 7A:
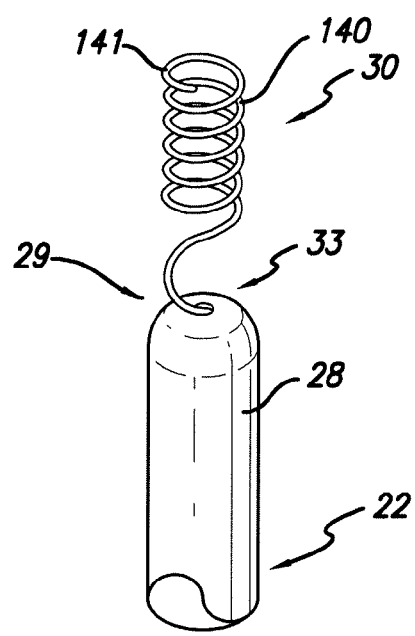
FIG. 7A is a partial side view of an alternative embodiment of the wire guide shown in FIG. 1.
Figure 7B:
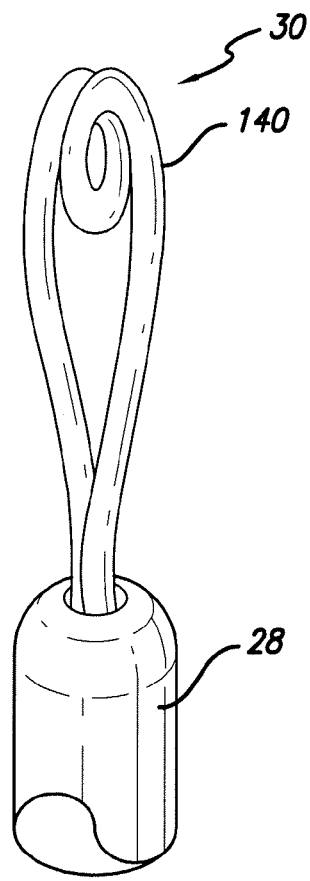
FIG. 7B is a partial side view of an alternative embodiment of the wire guide shown in FIG. 7A.

In some embodiments, the loop 30 may be provided as a helical coil configuration 140 as shown in FIG. 7. The coil 140 may be provided as an extension from an inner coil of the wire guide 20 (not shown) or the coil 140 may be provided separately and connected to the wire guide 20 using any method known to one skilled in the art. The coil 140 may be resiliently compressible for navigating though the body lumen. An end 141 of the coil 140 may be bent inwardly towards the center of the coil 140 so that the end 141 does not get caught in the lumen as the wire guide is being extended or retracted as shown in FIG. 7A. In some embodiments, both ends 141 of the coil 140 may be connected to the distal portion 28 of the shaft 22 as shown in FIG. 7B.

The loop 30 may also be formed as a die cut structure as shown in FIG. 8. The loop 30 having the connector 33 may be insert-molded, for example, from a polymer that has been molded onto the connector 29 at the distal portion 28 of the shaft 22 of the wire guide 20 connecting the loop 30 to the shaft 22. The polymer may form the connector 33 by being molded onto the connector 29 of the wire guide 20 within a mold 150. The mold 150 may include a form 152 to shape the polymer into the loop configuration. Alternatively, the polymer may be formed and solidified in the mold 150 and then the loop 30, including the connector 33, may be cut from the polymer using techniques known to one skilled in the art.

In some embodiments, the loop 30 may be formed from tubing 170 that may be molded or extruded in the desired shape for the loop 30. For example, as shown in FIG. 9A, the profile of the loop 30 includes the connector 33 shaped to fit with the connector 29 of shaft 22. The loop 30 may be formed in any shape with any shape connector 33. The tubing used to form the loop 30 may be injection molded, dipped, rotational molded, slush molded, fiber spun, blow molded, extruded or over molded to the desired form. The length of tubing 170 may be sectioned into individual loops 30 shown in FIG. 9B by cutting the tubing at the desired thickness. The loop 30 may be connected to the connector 29 of the shaft 22 by any method known to one skilled in the art. The tubing may be formed from any material, for example, PTFE. A coating layer may be included over the loop 30 at the connecting structure 32 to form the smooth outer surface 35.

Any method may be used to connect the connector 29 of the shaft 22 to the connector 33 of the loop 30. As described above, the connectors 29 and 33 may be sized and shaped to releasably interlock together the connectors 29 and 33 for example, by forming a snap-fit connection between the portions or by threading together the respective threads. In addition or as an alternative, the connectors 29 and 33 may be connected by bonding, including, but not limited to adhesive bonds and solder bonds, welding and molding. Combinations of these methods may also be used.

Any suitable material can be used for the wire guide 20 and portions thereof. The material chosen need only be biocompatible, or made biocompatible, and able to be formed into the structures described herein. Exemplary materials will also be compliant, elastic, resilient and have shape memory. Portions of the wire guide 20, such as the loop 30 and the shaft 22 may be made from different materials or the same materials. Examples of suitable materials include, but are not limited to stainless steel, tantalum, nitinol; gold, silver, tungsten, platinum, inconel, cobalt-chromium alloys and iridium, all of which are commercially available metals or alloys used in the fabrication of medical devices. Portions of the wire guide may be formed from a medically-acceptable polymer. For example, exemplary polymers include, but are not limited to, cellulose acetate, cellulose nitrate, silicone, polyethylene, high density polyethylene, polyethylene teraphthalate, polyurethane, polytetrafluoroethylene (PTFE), polyamide, polyester, polyorthoester, polyvinyl chloride (PVC), polypropylene, acrylonitrile-butadiene-styrene (ABS), polycarbonate, polyurethane, nylon silicone, and polyanhydride.

Portions of the wire guide 20 may also be made from a bioabsorbable material. A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes; polyisocyantes; polyphosphazines; polyethers including polyglycols polyorthoesters; expoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, poly-lysine, gelatin, fibrin, fibrinogen, casein, and collagen. For example, when the loop 30 is die-cut as described above, the loop 30 may be made from PTFE.

The wire guide 20, or portions thereof, may comprise a wire, a tubular member or a sheet of material. Further, the wire guide 20 or portions thereof may be formed from a series of layers, or as a coated core structure. For example, in one embodiment, the shaft 22 may comprise a nitinol core with a PTFE covering. The loop 30 may also be formed of nitinol and may include a PTFE covering. Portions of the loop 30 may also be reinforced for example, by providing additional layers of materials or stronger material from the list above, in or to prevent kinking. Any reinforcing materials will still allow the loop 30 to flex as it navigates through the lumen to the treatment site.

A variety of shapes and sizes of the shaft 22 and the loop 30 may be used, and these can both be optimized based on particular applications. The dimensions of the shaft 22 and the loop 30 will depend upon various factors, including the intended use of the wire guide 20 and the body lumens into which the wire guide 20 will be positioned. For a wire guide 20 intended to cannulate the common bile duct, suitable dimensions include a shaft diameter 39 of between approximately 0.016 inches and approximately 0.038 inches, and preferably comprises a diameter 39 of approximately 0.035 inches. The distal portion diameter 37 forming the loop 30 of the wire guide 20 preferably has a diameter of between approximately 0.003 inches and approximately 0.010 inches, and preferably comprises a diameter of approximately 0.006 inches. When the loop 30 is ovoid in shape and delivered to the bile duct, the length of the loop 30 may be between approximately 4 and approximately 5 millimeters, and the width 34 at the widest portion of the loop 30 may be between approximately 2 and approximately 3 millimeters. One skilled in the art will recognize that other sizes and shapes are possible depending on the bodily location the wire guide 20 is configured to enter. For example, the loop 30 may also be configured to enter the colon, pancreas and esophagus that may require different sizes than described above. Any size and shape loop 30 may be used with the present invention.

Coatings may also be applied to at least a portion of the wire guide 20. The coating(s) may be applied by dipping, molding, spraying, heat shrinking or extrusion of a suitable coating material, such as PTFE, polyolefin, polyvinyl chloride (PVC), polyester (PET) and fluorinated ethylene propylene (FEP) and/or other polymeric coatings, directly to the wire guide 20 or portions thereof. Bioabsorbable coatings may also be used.

In some embodiments, a thin heat shrinkable material may be used for the coating, such as PTFE. The heat shrinkable materials facilitate manufacturing while providing a lubricious coating, which facilitates navigation. In preferred embodiments, the thickness of the coating is between approximately 0.001 and 0.010 inches. In particularly preferred embodiments, the thickness of the coating is between approximately 0.001 and 0.005 inches. In still more preferred embodiments, the thickness of the coating is between approximately 0.001 and 0.002 inches. These preferred thicknesses provide suitable coatings while not adding significantly to the overall thickness of the device.

Also, the wire guide 20 or portions thereof, with or without the coating described above, may be treated with a hydrophilic coating or hybrid polymer mixture, such as those based on polyvinyl puroladine and cellulose esters in organic solvent solutions. These solutions make the wire guide particularly lubricious when in contact with body fluids, which aids in navigation.

Radiopaque materials may be added in the coating. Also, radiopaque materials known in the art may be placed on the shaft 22 and the loop 30 and other portions of the wire guide 20. Several examples of suitable radiopaque materials and markers are known in the art, and any suitable material and/or marker can be utilized in the present invention. Common radiopaque materials include barium sulfate, bismuth subcarbonate, and zirconium dioxide. Other radiopaque elements include: cadmium, tungsten, gold, tantalum, bismuth, platinum, iridium, and rhodium. In one embodiment, iodine may be employed for its radiopacity and antimicrobial properties. Radiopacity is typically determined by fluoroscope or x-ray film. Radiopaque, physiologically compatible materials include metals and alloys selected from the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biocompatible. For example, a platinum/tungsten alloy, e.g., 8% tungsten and the remainder platinum may be used.

Operation of the wire guide 20 of the present invention is similar to conventional wire guides known in the art. The wire guide 20 may be provided to the operator preassembled with the wire guide 20 loaded into a catheter, such as the catheter 40 shown in FIGS. 10A and 10B-C. The catheter may be any catheter known to one skilled in the art, including, but not limited to, dual lumen, triple lumen catheters, balloon catheters, stent delivery catheters, cannulae, papillotomes and sphincterotomes, and the like. In some embodiments, the wire guide 20 may be back loaded into the lumen 52 so that the distal portion 28 including the loop 30 of the wire guide 20 extends distally from the catheter 40. Back loading refers to introduction of the proximal portion 26 of the wire guide 20 into the catheter 40 until the distal portion 26 extends out of a proximal guide wire exit (FIG. 10A). The wire guide 20 may be oriented in any direction when assembled into the catheter 40. For example, when the wire guide 20 is back loaded into a catheter 40 having an offset lumen, the wire guide 20 may be oriented so that the loop 30 is generally centered with respect to the catheter 40. As shown in FIGS. 10B and 10C, the wire guide 20 may include radiopaque portions 70 for orienting the wire guide 20 as the wire guide 20 is navigated through the passageways. The radiopaque portions 70 may be any type of radiopaque marker known to one skilled in the art.

Figure 11A:
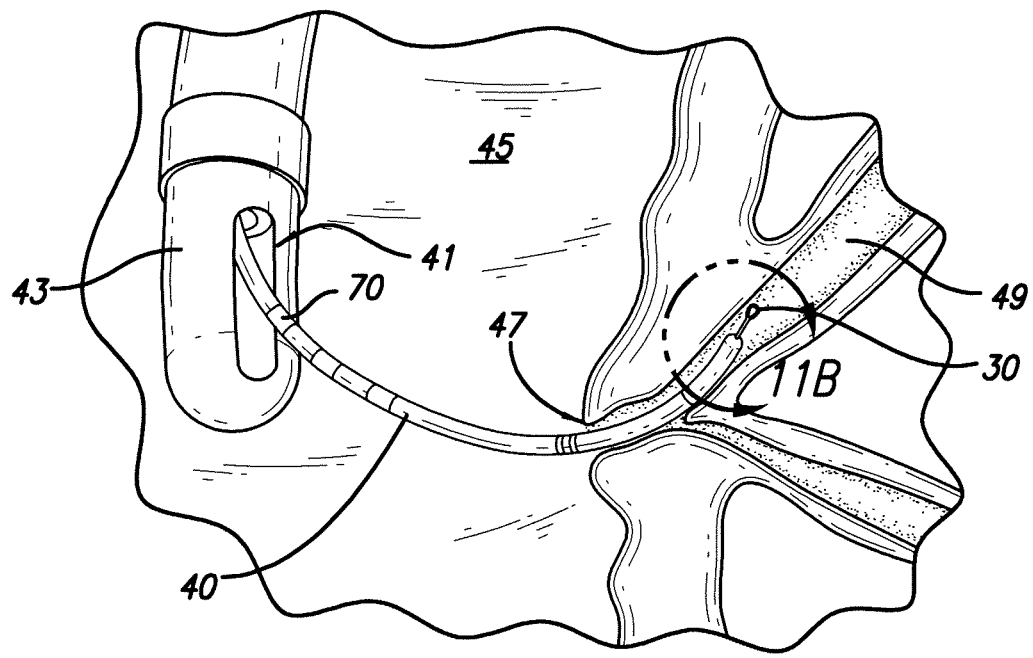
FIG. 11A illustrates the wire guide of the present invention entering the common bile duct.
Figure 11B:
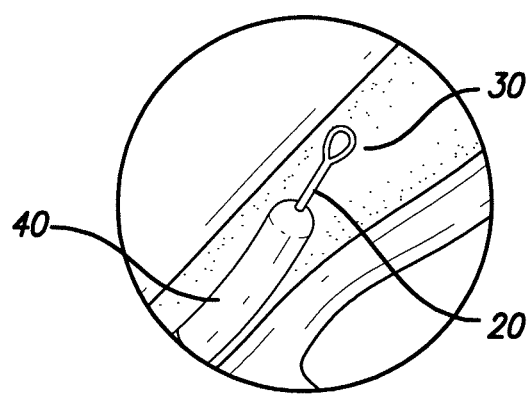
FIG. 11B is an enlarged view of the loop tip shown in FIG. 11A.

The wire guide 20 may be advanced through the tortuous body lumen to the desired location and the catheter 40 may be advanced over the wire guide 20 following standard procedures known to one skilled in the art. FIG. 11A illustrates the wire guide 20 extending out an opening 41 of an endoscope 43. The endoscope 43 is positioned in the duodenum 45 and the wire guide 20 is shown entering the biliary tree 49 through the ampullary orifice (Papilla of Vater) 47. FIG. 11B is an enlargement of the wire guide 20 moving through a torturous path 44 within a body vessel 60. The loop 30 deforms slightly in response to the torturous path 44. This allows the wire guide 20 to continue navigating along the interior of the body vessel 60. The catheter 40 may be introduced over the wire guide 20 to the treatment location.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. Unless otherwise indicated, all ordinary words and terms used herein shall take their customary meaning as defined in *The New Shorter Oxford English Dictionary*, 1993 *edition*. All technical terms shall take on their customary meaning as established by the appropriate technical discipline utilized by those normally skilled in that particular art area. All medical terms shall take their meaning as defined by *Stedman's Medical Dictionary*, 27*th edition*.

It is therefore intended that the foregoing detailed description be regarded as illustrative rather than limiting, and that it be understood that it is the following claims, including all equivalents, that are intended to define the spirit and scope of this invention.

The invention claimed is:

1. A wire guide configured for navigation through a lumen and for having a medical device advanced over the wire guide, the wire guide comprising:
   an elongate shaft comprising a proximal portion and a distal portion, the distal portion comprising a first interlocking connector at a distal end of the shaft, the distal portion having a first diameter; and
   a loop portion comprising a deformable loop having a continuous perimeter surrounding an opening defined therethrough and the loop portion comprising a second interlocking connector at a proximal end of the loop portion, the second interlocking connector extending proximally from the deformable loop and configured for connecting with the first interlocking connector of the shaft and forming a connection between the first interlocking connector and the second interlocking connector at the distal end of the shaft so that the deformable loop extends distal to the connection and the shaft when the first and second interlocking connectors are connected and the deformable loop having a second diameter defined at the widest portion of the perimeter that is greater than the first diameter;
   wherein the connection provides for transmission of torque from the proximal portion of the shaft to the loop along a longitudinal axis of the shaft and wherein the second interlocking connector is configured for removably connecting with the first interlocking connector so that the second interlocking connector is removable from the first interlocking connector with the wire guide position within the lumen.

2. The wire guide of claim 1, wherein one of the first interlocking connector and the second interlocking connector comprises a protrusion and the other of the first interlocking connector and the second interlocking connector comprises a receptacle.

3. The wire guide of claim 1, wherein the first interlocking connector and the second interlocking connector are threaded.

4. The wire guide of claim 1, wherein the loop portion comprises a folding region.

5. The wire guide of claim 1, wherein at least a portion of the wire guide comprises a bioabsorbable material.

6. The wire guide of claim 1, wherein at least a portion of the wire guide comprises a polymer.

7. The wire guide of claim 1, wherein at least a portion of the wire guide comprises nitinol.

8. The wire guide of claim 1, wherein at least a portion of the wire guide further comprises a coating.

9. The wire guide of claim 1, wherein the wire guide comprises a coating covering at least the first interlocking connector and the second interlocking connector for forming a smooth outer surface.

10. A wire guide system comprising:
   a catheter comprising a proximal portion and a distal portion; and
   a wire guide extending from the distal portion of the catheter, the wire guide configured for navigation through a lumen and for having a medical device advanced over the wire guide the wire guide comprising:
   an elongate shaft comprising a proximal portion and a distal portion, the distal portion comprising a first interlocking connector at a distal end of the shaft; and
   a loop portion comprising a deformable loop having a continuous perimeter surrounding an opening defined therethrough and a second interlocking connector at a proximal end of the loop portion extending proximally from the deformable loop, the second interlocking connector configured for connecting to the first interlocking connector and forming a connection at the distal end of the shaft so that the deformable loop extends distal to the connection and the shaft when the first and second interlocking connectors are connected, the deformable loop having a diameter greater than a diameter of the distal portion of the shaft;
   wherein the connection provides for transmission of torque from the proximal portion of the shaft to the loop along a longitudinal axis of the shaft and wherein the second interlocking, connector is configured for removably connecting with the first interlocking connector so that the second interlocking connector is removable from the first interlocking, connector with the wire guide positioned within the lumen by contacting a portion of the loop with a portion of the catheter.

11. The system of claim 10, wherein the wire guide further comprises a snap-fit connection between the first interlocking connector and the second interlocking connector.

12. A method of manufacturing a wire guide having a loop tip, the wire guide configured for navigation through a lumen and for having a medical device advanced over the wire guide the method comprising:
   forming an elongate shaft having a proximal portion and a distal portion; the distal portion including a first interlocking connector at a distal end of the shaft;
   forming a loop structure having a deformable loop having a continuous perimeter surrounding an opening defined therethrough and a diameter greater than a diameter of the distal portion of the shaft, and the loop structure comprising a second interlocking connector at a proximal end of the loop portion extending proximally from the deformable loop;
   connecting the first interlocking connector of the shaft to the second interlocking connector of the loop; and
   forming a connection between the first interlocking connector and the second interlocking connector at the distal end of the shaft so that the deformable loop extends distal to the connection and the shaft and so that the connection provides for transmission of torque from the proximal portion of the shaft to the loop along a longitudinal axis of the shaft and the second interlocking connector is configured for removably connecting with the first interlocking connector so that the second interlocking connector is removable from the first interlocking connector with the wire guide positioned within the lumen.

13. The method of claim 12 wherein the loop is formed by molding or extrusion.

14. The method of claim 12, further comprising providing a catheter and back loading the wire guide into the catheter.

15. The method of claim 12, further comprising providing a radiopaque material on at least a portion of the wire guide.

16. The wire guide of claim 1, wherein the connection is a snap-fit connection.

17. The system of claim 10, wherein the loop portion comprises a folding region.

18. The system of claim 10, wherein the wire guide comprises a coating covering at least the first interlocking connector and the second interlocking connector for forming a smooth outer surface.

19. The wire guide of claim 1, wherein at least a portion of the loop portion comprises a bioabsorbable material.

20. The system of claim 10, wherein at least a portion of the loop portion comprises a bioabsorbable material.

* * * * *

UNITED STATES PATENT AND TRADEMARK OFFICE
CERTIFICATE OF CORRECTION

PATENT NO.        : 8,715,205 B2                    Page 1 of 1
APPLICATION NO.   : 11/841175
DATED             : May 6, 2014
INVENTOR(S)       : Matthew P. Carter et al.

It is certified that error appears in the above-identified patent and that said Letters Patent is hereby corrected as shown below:

<u>In the Claims</u>

In column 10, claim 1, line 14, after "with the wire guide" replace "position" with --positioned--.

Signed and Sealed this
Fifth Day of April, 2016

Michelle K. Lee
*Director of the United States Patent and Trademark Office*